United States Patent
Yeh et al.

(10) Patent No.: US 7,041,815 B2
(45) Date of Patent: May 9, 2006

(54) SPORAMIN PROMOTER AND USES THEREOF

(75) Inventors: Kai-Wun Yeh, Taipei (TW); Shu-Jen Wang, Taipei (TW)

(73) Assignee: Sinon Corporation, Taichung Hsien (TW)

( * ) Notice: Subject to any disclaimer, the term of this patent is extended or adjusted under 35 U.S.C. 154(b) by 562 days.

(21) Appl. No.: 10/140,896

(22) Filed: May 8, 2002

(65) Prior Publication Data

US 2003/0167518 A1 Sep. 4, 2003

Related U.S. Application Data

(60) Provisional application No. 60/289,630, filed on May 8, 2001.

(51) Int. Cl.
*C12N 15/11* (2006.01)
*C12N 5/04* (2006.01)
*C07H 21/04* (2006.01)
*C12P 21/06* (2006.01)
*A01H 5/00* (2006.01)

(52) U.S. Cl. .................. 536/24.1; 536/23.1; 435/69.1; 435/419; 435/430; 435/425; 800/298; 800/317.3

(58) Field of Classification Search ............... 536/23.1, 536/24.1; 800/298, 317.3; 435/69.1, 419, 435/425, 430
See application file for complete search history.

(56) References Cited

U.S. PATENT DOCUMENTS 5,110,732 A * 5/1992 Benfey et al. .............. 800/287

OTHER PUBLICATIONS

Oommenn et al (1994, The Plant Cell 6: 1789-1803).*
X13509 GENBANK Report (reportedly available on Apr. 21, 1993).
X13510 GENBANK Report (reportedly available on Apr. 21, 1993).

* cited by examiner

*Primary Examiner*—Elizabeth McElwain
*Assistant Examiner*—Georgia Helmer
(74) *Attorney, Agent, or Firm*—Fish & Richardson P.C.

(57) ABSTRACT

The invention features sporamin promoters, including the promoter of the *Ipomoea batatas* sporamin A gene. The promoter directs gene expression in tubers and responds in aerial structures to wounding, pathogens, and other environmental insults.

26 Claims, No Drawings

SEQUENCE LISTING

<160> NUMBER OF SEQ ID NOS: 5

<210> SEQ ID NO 1
<211> LENGTH: 1283
<212> TYPE: DNA
<213> ORGANISM: Ipomoea batatas

<400> SEQUENCE: 1

```
cgacggcccg ggctaggtca agtaacccga acttggtcaa gtttgttata acttattctc    60
cctttttcgt gagggcggtt aggggactta gtataaatag gagtgtaatc gggcttgtta   120
agacatattg aactcacctg taatagcatt acatttctcg taaatacgta caatatcctt   180
gtctttccaa taacattttt gtcttttacc attatctttt atccaatcct ttaattatcg   240
agtttgttaa ttcagatcac ccaaattaat taaatccatc atttggatta agttatctta   300
ctttactaat tagagttttt atcttcagag gaaggaagaa gaaaattaat tgacatgact   360
ctcatcgggt tgcactccac ccattatgtt atacaatgca aactctttta aaataaatta   420
aaattatata tatatataat agtgcaacct acatcacttt ttcaatgtgg gacgaaagca   480
ccttcaaaag tctttcgaac cccatttttc ctcgaatata ttttgagaat caatttctca   540
attaatcatt attatccatc ttcgtgtaca tatataatat atatatcaca ttaaacatct   600
aacttagaag aactcaaatt tattttttaac tctacttata tcaaaagtgg actctactga   660
aaattatacc acaaaatgat attttaaacg ttatatttaa caaaaatttc tgacattatc   720
ttatttaatc ttctactagt tagaataata aaacaaattt cactcataac ataaatttaa   780
atagtgatcg tgaattttta cggaaattaa tcaaataatt gtatgtaata atgtaatgta   840
atgaattttg atgatgggta aaatgtattt taattattac acgacttgcc ttctttaatt   900
tgttcttagg atcctagact tcatccctgc atagcaaaac cattggacac ttggacggcc   960
acaaatcatt tctattttct cccaactcct cctgtcagca tgggatcatt atcaacttta  1020
tctcatccca ttacacaccg taagtgtacc atccatcgct caatcactgt atacttaaat  1080
ctccagatta agtcactaaa taactgtgtt ggactgtgaa actttgagt aaaaaaggc    1140 aaaatactct taaaactgta caaaaaacaa taattcaacc cttactcttg ttgtctataa  1200
attggatgca tgagagctca acacaacaca acaccaccaa caaattaaac atcattacct  1260
```

-continued

```
cttagctttt ctcccaagtt gtc                                         1283
```

<210> SEQ ID NO 2
<211> LENGTH: 271
<212> TYPE: DNA
<213> ORGANISM: Ipomoea batatas

<400> SEQUENCE: 2

```
cgacggcccg ggctaggtca agtaacccga acttggtcaa gtttgttata acttattctc    60
cctttttcgt gagggcggtt aggggactta gtataaatag gagtgtaatc gggcttgtta   120
agacatattg aactcacctg taatagcatt acatttctcg taaatacgta caatatcctt   180
gtctttccaa taacattttt gtcttttacc attatctttt atccaatcct ttaattatcg   240
agtttgttaa ttcagatcac ccaaattaat t                                  271
```

<210> SEQ ID NO 3
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 3

```
gaacttggga gaaaagctaa g                                              21
```

<210> SEQ ID NO 4
<211> LENGTH: 12
<212> TYPE: DNA
<213> ORGANISM: Ipomoea batatas

<400> SEQUENCE: 4

```
cgaaagcacc tt                                                        12
```

<210> SEQ ID NO 5
<211> LENGTH: 12
<212> TYPE: DNA
<213> ORGANISM: Ipomoea batatas

<400> SEQUENCE: 5

```
gtaaaatacg ta                                                        12
```

SPORAMIN PROMOTER AND USES THEREOF

CROSS REFERENCE TO RELATED APPLICATIONS

Pursuant to 35 USC § 119(e), this application claims the benefit of prior U.S. provisional application 60/289,630, filed May 8, 2001.

BACKGROUND OF THE INVENTION

The advent of modern biotechnological methods has facilitated the genetic modification of plants. One particularly valuable genetic modification is transgenesis, the insertion of recombinant nucleic acids into plants. One exemplary application is the production of a biological compound of medical, industrial, or commercial value. A second arena of applications is enhancement of plant defenses against environmental insults and pathogens. Given the fundamental and primordial role of plants as a source of nutrition and natural materials, the ability to enhance the properties of plants thorough engineering has tremendous medical and economic value.

SUMMARY OF THE INVENTION

The invention features the sweet potato sporamin promoter and related promoters. The invention is based, in part, on the discovery of nucleic acid which contains the sporamin promoter, and the finding that, in addition to directing transcription in sweet potato tubers, the promoter is activated in response to wounding in leaves, e.g., mechanically wounded leaves. The promoter activates expression of a heterologous coding sequence in wounded leaves, and in methyl jasmonate-treated leaves. Moreover, the sporamin promoter is also functional in non-tuberous plants, e.g., in tobacco plants. The sequence of the sporamin promoter is shown below:

```
-1253  CGACGGCCCG GGCTAGGTCA AGTAACCCGA ACTTGGTCAA GTTTGTTATA

-1203  ACTTATTCTC CCTTTTTCGT GAGGGCGGTT AGGGGACTTA GTATAAATAG

-1153  GAGTGTAATC GGGCTTGTTA AGACATATTG AACTCACCTG TAATAGCATT

-1103  ACATTTCTCG TAAATACGTA CAATATCCTT GTCTTTCCAA TAACATTTTT

-1053  GTCTTTTACC ATTATCTTTT ATCCAATCCT TTAATTATCG AGTTTGTTAA

-1003  TTCAGATCAC CCAAATTAAT TAAATCCATC ATTTGGATTA AGTTATCTTA

-953  CTTTACTAAT TAGAGTTTTT ATCTTCAGAG GAAGGAAGAA GAAAATTAAT

-903  TGACATGACT CTCATCGGGT TGCACTCCAC CCATTATGTT ATACAATGCA

-853  AACTCTTTTA AAATAAATTA AAATTATATA TATATATAAT AGTGCAACCT

-803  ACATCACTTT TTCAATGTGG GACGAAAGCA CCTTCAAAAG TCTTTCGAAC

-753  CCCATTTTTC CTCGAATATA TTTTGAGAAT CAATTTCTCA ATTAATCATT

-703  ATTATCCATC TTCGTGTACA TATATAATAT ATATATCACA TTAAACATCT

-653  AACTTAGAAG AACTCAAATT TATTTTTAAC TCTACTTATA TCAAAAGTGG

-603  ACTCTACTGA AAATTATACC ACAAAATGAT ATTTTAAACG TTATATTTAA

-553  CAAAAATTTC TGACATTATC TTATTTAATC TTCTACTAGT TAGAATAATA

-503  AAACAAATTT CACTCATAAC ATAAATTTAA ATAGTGATCG TGAATTTTTA

-453  CGGAAATTAA TCAAATAATT GTATGTAATA ATGTAATGTA ATGAATTTTG

-403  ATGATGGGTA AAATGTATTT TAATTATTAC ACGACTTGCC TTCTTTAATT

-353  TCTTCTTAGG ATCCTAGACT TCATCCCTGC ATAGCAAAAC CATTGGACAC

-303  TTGGACGGCC ACAAATCATT TCTATTTTCT CCCAACTCCT CCTGTCAGCA

-253  TGGGATCATT ATCAACTTTA TCTCATCCCA TTACACACCG TAAGTGTACC

-203  ATCCATCGCT CAATCACTGT ATACTTAAAT CTCCAGATTA AGTCACTAAA

-153  TAACTGTGTT GGACTCTGAA AACTTTGAGT AAAAAAAGGC AAAATACTCT

-103  TAAAACTGTA CAAAAAACAA TAATTCAACC CTTACTCTTG TTGTCTATAA

-53  ATTGGATGCA TGAGAGCTCA ACACAACACA ACACCACCAA CAAATTAAAC

-3  ATCATTACCT CTTAGCTTTT CTCCCAAGTT GTC  30
```

The full promoter sequence is recited as SEQ ID NO:1 and is also referred to as "Pspoa." The region from nucleotides −1253 to −983 of SEQ ID NO:1 is designated as SEQ ID NO:2. Underscored promoter elements are respectively: a G-box-like element, a nos wounding response element, a PI-II wound response element, a GCC core-like sequence, a sucrose response element, a CAAT box, an SP8a box, a TATA box, and the transcription start site (+1) (An et al. (1990) *Plant Cell* 2:225–233; Palm et al. (1990) *Proc. Natl. Acad. Sci. USA* 87:603–607).

Accordingly, the invention features an isolated nucleic acid including SEQ ID NO:1, a promoter that hybridizes under stringent conditions to SEQ ID NO:1, and a promoter that is at least 60% (e.g., 60%, 70%, 80%, 85%, 90%, 92%, 95%, 98% or 99% or more) identical to SEQ ID NO:1. A promoter of the invention can direct gene expression of operably linked genes in leaves upon wounding, e.g., upon mechanical wounding or upon wounding by pest or pathogen attack. Alternatively, the promoter can direct gene expression in tubers. The nucleic acid can further include a heterologous sequence which is operably linked to the promoter. The heterologous sequence can encode a polypeptide, such as a polypeptide with bacteriocidal, fungicidal, or insecticidal activity. For example, the polypeptide can be a protease inhibitor, collagenase, chitinase, glucanase, glycosidase, or *Bacillus thuringiensis* δ-endotoxin. Alternatively the polypeptide can be a protein that protects a plant tissue against injury, e.g., a chaperone, anti-freeze protein, thioredoxin, or glutathione reductases. The invention also features nucleic acids including a fragment of SEQ ID NO:1, e.g., a fragment of at least 10, 15, 20, 50, 100, 500, or more nucleotides in length.

In another aspect, the invention features an isolated nucleic acid including SEQ ID NO:2, a promoter that hybridizes under stringent conditions to SEQ ID NO:2, and a promoter that is at least 60% (e.g., 60%, 70%, 80%, 85%, 90%, 92%, 95%, or 98% or more) identical to SEQ ID NO:2. Such isolated nucleic acids can direct gene expression in response to wounding, as described above, or in tubers. The nucleic acid can be operably linked to a heterologous sequence, e.g., a nucleic acid sequence described above.

The nucleic acids of the invention can be included in a vector, e.g., in a vector containing T-DNA border sequences designed to facilitate transformation into plant cells using the *Agrobacterium* method, described below. The invention also includes transformed cells, e.g., transformed plant cells, which contain the isolated nucleic acids of the invention, transgenic plants derived from such cells, as well as seeds and progeny of such plants. The plant can be a dicot or a monocot. For example, the plant can be a *Ipomoea batatas, Arabidopsis,* rice, tobacco, maize, *Brassica,* or potato plant.

The invention also provides a method of protecting a plant or plant tissue from a pathogen or a pest. The method includes transforming a plant cell with a nucleic acid of the invention, and cultivating the cell to produce a plant. The nucleic acid can express a polypeptide with anti-bacterial, anti-fungal, anti-insect, or anti-nematode properties in response to a wounding event to thereby protect the plant or plant tissue, e.g., an isolated tuber. Alternatively, the polypeptide can provide protection against environmental or physical stress, e.g., heat or cold, bruising, and so forth.

Additionally, the invention provides a method of producing a polypeptide. The method includes transforming a plant cell with a promoter of the invention operably linked to a nucleic acid sequence coding for the polypeptide, and cultivating the cell to produce a plant. In one implementation, the method further includes: (1) contacting the plant with an elicitor that activates the promoter, e.g., methyl jasmonate, (2) applying a pest or pathogen, or (3) wounding the plant, e.g., mechanically. The plant can be harvested and the polypeptide can be extracted and/or purified from the harvested plant. In an alternative implementation, the promoter can direct polypeptide expression in tubers of the plants. The tubers can be harvested and the polypeptide can be extracted and/or purified from the tubers.

The invention also provides a post-harvest polypeptide production method wherein the above-described plant is harvested prior to contacting the plant with an elicitor, pest, or pathogen, or prior to mechanical wounding. The polypeptide can be extracted and/or purified from the so-treated harvested material.

In still another aspect, the invention features a kit including a vector containing a sporamin promoter, e.g., containing SEQ ID NO:1 or SEQ ID NO:2, or fragments thereof larger than 20 nucleotides. The vector can further contain a selectable marker, and a restriction enzyme polylinker such that insertion of a coding nucleic acid sequence into the polylinker operably links it to the promoter.

An "isolated nucleic acid" is a nucleic acid which has a non-naturally occurring sequence, or which has the sequence of part or all of a naturally occurring gene but is free of the genes that flank the naturally occurring gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment. It also includes a recombinant nucleotide sequence that is part of a hybrid gene, i.e., a gene encoding a fusion protein. Specifically excluded from this definition are mixtures of DNA molecules, vectors, or clones as they occur in a DNA library such as a cDNA or genomic DNA library. Also excluded are RNA molecules that consist of naturally occurring sequences (e.g., naturally occurring mRNA), except where the RNA is in a purified state such that it is at least 90% free of other naturally occurring RNA species. Thus, a naturally occurring mRNA in a whole mRNA preparation prepared from a cell would not be an "isolated nucleic acid," but a single mRNA species purified to 90% homogeneity from that whole mRNA preparation would be.

As used herein, "percent identity" of two nucleic acids is determined using the algorithm of Karlin and Altschul (*Proc. Natl. Acad. Sci. USA* 87:2264–2268, 1990), modified as in Karlin and Altschul (*Proc. Natl. Acad. Sci. USA* 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12 to obtain nucleotide sequences homologous to a nucleic acid molecules of the invention. To obtain gapped alignments for comparison purposes, Gapped BLAST is utilized as described in Altschul et al. (*Nucleic Acids Res.* 25:3389–3402, 1997). When utilizing BLAST and Gapped BLAST programs, the default parameters of the respective programs (e.g., XBLAST and NBLAST) are used (see, e.g., National Center for Biotechnology Information, National Institutes of Health, Bethesda Md.).

By "hybridizes under stringent conditions" is meant specific and non-covalent equilibrium binding by base-pairing to an immobilized reference nucleic acid in a hybridization solution containing 0.2×SSC (1.75 g/l NaCl, 0.88 g/l Na$_3$citrate.2H$_2$O; pH 7.0) and 0.1% (w/v) sodium dodecylsulfate at 68° C. Washings, if any are required to achieve equilibrium, are carried out with the hybridization solution.

A "heterologous sequence" is a nucleotide sequence that is not naturally operably linked to the sporamin promoter in a naturally occurring organism.

A "promoter" is a nucleotide sequence that is capable of directing transcription in at least one context, e.g., when it is operably linked to a heterologous sequence in a plasmid within a plant cell. In other words, a promoter can exist without downstream sequences to transcribe, so long as the promoter sequence can direct transcription when placed upstream of a heterologous sequence in a different context.

As used herein, the term "wounding" refers to an event in which a cell or tissue is damaged, e.g., by mechanical stress or insult. The stress includes physical pressure, shearing, dehydration, heat, or cold. The stress can result from environmental conditions or from another organism, e.g., a pathogen, a pest or another animal. To determine if a promoter of the invention responds to wounding, a plant tissue, e.g., a leaf, can be cut with a razor or scissors. As used herein, a "pathogen" is a virus, bacteria, protist, or fungi, which can infect a plant and cause damage to a plant cell or tissue. A "pest" refers to an animal, e.g., a nematode, insect, bird, rodent, or other animal, that damages a plant cell or plant tissue, especially as part of a behavior of the pest, e.g., diet, nesting, etc.

As used herein, an "elicitor" is a compound, e.g., a naturally occurring compound, which activates gene expression in a plant. Elicitors include methyl jasmonate, salicylic acid, ethylene, absiscic acid, gibberillins, HgCl$_2$, and H$_2$O$_2$.

A "transgene" refers to a nucleic acid containing a gene (i.e., a promoter operably linked to a sequence to be transcribed) which is introduced into a cell by artifice. As used herein, the term "transgenic cell" refers to a cell containing a transgene. As used herein, a "transgenic plant" is a plant in which one or more, or all, of the cells of the plant contain a transgene. The transgene can be introduced into the cell, directly or indirectly by introduction into a precursor of the cell, by way of deliberate genetic manipulation, such as by microinjection or by infection with a recombinant virus.

An "anti-bacterial," "anti-fungal," "anti-insect," or "anti-nematode," activity refers to a capability of reducing the growth or viability of the respective biologic by at least 40%, 50%, 60%, 70%, 80% or more, e.g., relative to an untreated control.

Sporamin proteins account for approximately 85% of the total soluble protein in tubers. The sporamin promoter directs the high and specific expression of sporamin protein in tubers. Thus, the sporamin promoter can be used to direct the abundant expression of heterologous proteins in tubers. Such an application is of immense benefit for the pharmaceutical production or polypeptide with medical applications, and the industrial production of enzymes, to mention but a couple uses.

The sporamin promoter, described herein, is also induced by wounding and by an elicitor, methyl jasmonate. The sporamin promoter, therefore, enables methods of applying an elicitor, i.e., methyl jasmonate, to induce production of a heterologous polypeptide. Moreover, heterologous polypeptides can include biosynthetic enzymes which produce secondary metabolites. Finally, because the sporamin promoter is activated in response to plant wounding, the promoter can be operably linked to a polypeptide which minimizes damage on wounding or which provides defenses against a wounding agent, e.g., a pest or pathogen. Such an application which improves the resistance of plants to assault by pathogens and the environment stands to provide immeasurable benefits.

Other features, objects, and advantages of the invention will be apparent from the description and from the claims.

DETAILED DESCRIPTION

Promoters that direct gene transcription in tubers can be isolated by identifying cDNAs of genes transcribed in tubers, and isolating genomic DNA upstream of the cDNA. Genes or proteins known to be expressed in response to wounding, environmental stress, or pathogen attack or infection, likewise, provide a source or promoters which are active under such conditions.

Methods for Isolating Promoters

A host of methods are known in the art for isolating promoters from genomic DNA (see, for example, Sambrook et al. (1989) *Molecular Cloning: A Laboratory Manual.* Cold Spring Harbor Laboratory Press, Cold Spring Harbor, N.Y.).

Genomic DNA isolation. Genomic DNA was isolated as follows. A sample of tuberous roots (20 g) was ground in liquid nitrogen, transferred into a flask containing 50 ml of extraction buffer (100 mM Tris-HCl, pH 8.0, 50 mM EDTA, 500 mM NaCl, 100 µg proteinase K ml$^{-1}$), and then incubated at room temperature with gentle shaking for 20 minutes before centrifugation at 12,000 g for 10 min. The supernatant received 3 ml of 20% (w/v) SDS, was incubated at 55° C. for 1 hr, and then centrifuged at 12,000 g for 20 min. After centrifugation, the supernatant was mixed with 0.1 volume of 3 M potassium acetate (pH 5.2) and 0.6 volume of isopropanol; the mixture was kept at −20° C. for 30 minutes before centrifugation at 12,000 g for 10 min at 4° C. The pellet containing DNA was dissolved in 2 ml of TE buffer (10 mM Tris—0.1 mM EDTA) before re-extracting in succession with equal volume of phenol/chloroform/isoamylalcohol (25:24:1, v/v) and chloroform/isoamylalcohol (24:1, v/v). After centrifugation, DNA in the supernatant was precipitated with 5 ml of 100% ethanol and 0.2 ml of 3 M sodium acetate, pH 5.2. Finally, the DNA pellet was dissolved in 0.5 ml of TE buffer or H$_2$O.

Screening Genomic DNA libraries. A wound-responsive promoter can be isolated from a genomic DNA library, e.g., an *Arabidopsis* genomic library, a tobacco genomic library, or an *Ipomoea batatas* genomic library. Isolated genomic DNA can be used to generate a genomic library. Methods for generating and screening such libraries are routine in the art (see, e.g., Sambrook et al. supra.; Benton and Davis (1977) *Science* 196:180; Grunstein and Hogness (1975) *Proc. Nat. Acad. Sci. USA.* 72:3961–3965). Plant genomic DNA can be sheared, e.g., by sonication, or by extrusion through a narrow pore. Alternatively, the DNA can be digested with a restriction enzyme. The digest can be done under conditions that favor partial digestion, such that not every recognition site is restricted. The digested and/or sheared genomic DNA can be size selected and then ligated into a host vector, e.g., into a plasmid, cosmid, YAC, BAC, bacteriophage genome, or P1. The ligation products can be transformed into an appropriate host cell, e.g., an *E. coli* cell, or a *Saccharomyces cerevisiae* cell. Alternatively the ligation products can be packaged into a virus, e.g., a bacteriophage. The library can be stored, e.g., frozen as appropriate. Alternatively, the library can be amplified. The library can be screened to identify a wound-responsive promoter. For example, nucleic acid containing sequences within a cDNA, encoding a protein induced by wounding, can be used as probe. The nucleic acid can be radiolabeled, or labeled with a fluorophore, or an chemical handle, e.g. a moiety recognized specifically and avidly by a protein (e.g. digoxygenin or biotin). The library can be probed for clones containing sequences which hybridize to the cDNA. Such clones can be further characterized by isolating the library DNA, restriction mapping, and nucleic acid sequencing as appropriate. The location of the cDNA sequence can be determined relative to the genomic DNA sequence. The promoter is located 5' to the first 5' nucleotide of the cDNA in the genomic sequence.

PCR Amplification. Alternatively, a promoter can be amplified from isolated genomic DNA using PCR. Guides for utilizing PCR are available, for example, Gelfind, 1989, PCR Technology. Principles and Applications for DNA Amplification, Ed., H. A. Erlich, Stockton Press, N.Y., and Current Protocol in Molecular Biology, Vol. 2, Ch. 15, Eds. Ausubel et al., John Wiley & Sons, 1988. PCR can be utilized to obtain a desired plant promoter. One PCR-based method is the "primer walking" method of Siebert et al. (1995) *Nucleic Acids Res.* 23:1087–1088, which is described as follows. Isolated plant genomic DNA is digested with a restriction enzyme which leaves blunt DNA ends. The digest genomic DNA is ligated to a synthetic adaptor molecule of the design elucidated in Siebert et al., supra. One strand contains a rare cutting restriction enzyme site, e.g., NotI; the second strand is shorter and ends in a 3' amine group, which cannot be extending by DNA polymerases. When the two strands are annealed, one terminus of the duplex is a flush or "blunt" end which can be ligated to the restricted genomic DNA. After adaptor ligation, PCR is used to amplify the promoter in a reaction containing a first primer and a second primer. The first primer is designed such that the primer is located near or at the 5'-most end of the cDNA induced by wounding and/or of the available genomic clone hybridizing to the cDNA. The second primer has a design such that it preferentially anneals to the outer region of the adaptor, but is prevented from annealing to DNA strands containing adaptors at both ternini (Siebert et al., supra.). Thus, amplification of a nucleic acid fragment containing one terminus in the desired gene is favored. The amplified promoter fragment can be cloned into a suitable vector, and verified by restriction analysis and nucleic acid sequencing.

Synthetic methods. A wound-responsive promoter, e.g., a sporamin-related promoter, can also be synthesized. It is routine in the art to synthesize oligonucleotides with specific sequence compositions. A set of oligonucleotides of 70–90 base pairs can be designed and constructed such that the oligonucleotides are partially overlapping and span the desired sporamin promoter. The overlap regions are approximately 15 base pairs in length and are designed to facilitate annealing of sequential oligonucleotides to each other. Once synthesized and purified, the oligonucleotides can be assembled. Sequential pairs of oligonucleotides can be annealed to each other, and synthesized into double-stranded nucleic acid cassettes using a DNA polymerase. Cassettes can be joined, either with engineered restriction sites, or again by including overlapping annealing regions. Two double stranded cassettes can be denatured, annealed, and amplified with the polymerase chain in reaction containing primers flanking the distal border of each cassette. A skilled artisan can apply these methods or variations thereof to construct the desired promoter sequence from synthetic oligonucleotides.

Identifying Promoter Elements

Regulatory elements in a wound-responsive promoter, e.g., sporamin-related promoters, can be identified by various methods known in the art.

Computer Searches. Once the sequence of a promoter is obtained, it can be stored in a computer-readable format. Known regulatory elements can be identified within the promoter sequence. For example, pattern match programs and modules of the Wisconsin GCG sequence analysis package are used to locate nucleotide sequences with perfect and imperfect matches to a consensus element. AlignAce 3.0 (Roth et al. (1998) *Nat. Biotechnol.* 16:939–45) and the Staden package (Staden (1994) *Methods Mol Biol.* 25:93–102) are examples of computer programs designed to recognize regulatory elements. Further, one skilled in the art of computer program can generate simple scripts using the PERL programming language to detect patterns, degenerate patterns, patterns with variable spacing, and repeats (Wall et al. (2000) *Programming Perl, 3rd Edition.* O'Reilly & Associates, Inc.). Such programs can be used to methodically search a promoter for elements known in the art.

Biochemical Studies. Biochemical techniques can identify nucleic acid elements that are binding sites for regulatory proteins. Lysates are prepared from cells in which a sporamin-related gene is known to be expressed, e.g., cells treated with methyl jasmonate or tuber cells. The clarified lysates are bound to labeled promoter DNA. Subsequently, the DNA is exposed to varying concentrations of a DNA cleaving agents, e.g., a chemical agent or Dnase I enzyme. The region of DNA protected from cleavage is identified on an 8% denaturing acrylamide gel. Protected regions can define a promoter element An additional method for defining elements in the sporamin promoter utilizes an in vivo activity assay. The promoter is resected from the 5' or 3'end with a restriction enzyme or an exonuclease. The resected fragment is cloned into a reporter vector, e.g. a vector containing the β-glucuronidase (GUS) enzyme reporter. The promoter fragments are analyzed either in the context of a heterologous promoter or the sporamin promoter. In the latter case, the GUS reporter gene is fused to the sporamin open reading frame, and the wild-type sporamin promoter is replaced with resected promoter fragments. In the former case, a heterologous promoter such as the "minimal" CaMV 35S promoter, which is truncated at nucleotide –46 relative to the mRNA start site (Skriver et al. (1991) *Proc. Natl. Acad. Sci. USA* 88:7266–7270) is used. The resected promoter fragments are inserted 5' of the minimal promoter. The reporter gene constructions are then transformed into plants cells using methods described below. Reporter gene transcription is monitored, particularly for appropriate regulatory activity, e.g., the transcription is monitored after cell wounding or methyl jasmonate treatment.

Identification of regulatory elements enables one skilled in the art to modify or construct additional promoters with desired regulatory properties, for example with a subset of properties of the sporamin promoter described herein. In addition, "hybrid" or "chimeric" promoters can be constructed by combining desired regulatory elements from the sporamin promoter with elements from another promoter, e.g., the nos promoter derived from the nopaline synthase promoter (Aryan et al. (1991), *Mol Gen. Genet.* 225:65–71). Additional examples of chimeric promoters are set forth below.

Gene Expression Analysis

The expression of a nucleic acid sequence operably linked to the sporamin promoter can be monitored by various methods routine in the art, including Northern analysis and reverse transcriptase-polymerase chain reaction (RT-PCR). The sequence can be that of an endogenous sporamin-related gene, or a heterologous sequence operably linked to the sporamin promoter.

Plant RNA Isolation. To isolate RNA from plant tissues, the tissues are first prepared and dissected. In addition, plants can be treated at various time intervals before sample collection, e.g., by wounding or by application of an elicitor. Total RNA is then extracted from the isolated plant tissues. Total RNA can be extracted by the rapid guanidinium hydrochloride-sarcosinate method as described in Yeh et al (1991) Focus 13:102–102. Samples of leaves (0.2 g) were ground in liquid nitrogen and the powder was mixed with 2 ml of extraction buffer (7.5 M guanidine hydrochloride, 25 mM sodium citrate, 0.5% [w/v] lauroyl sarcosine and 0.1 M β-mercaptoethanol). The mixture was incubated at room temperature for 10 minutes before centrifugation at 12,000 g for 10 min. The supernatant was treated in succession with equal volume of phenol/chloroform/isoamylalcohol (25:24:1, v/v) and chloroform/isoamylalcohol (24:1, v/v). RNA was precipitated with 5 ml of 100% ethanol and 0.2 ml of 3 M sodium acetate, pH 5.2, at −70° C. for 30 min. After centrifuigation, the pellet was dissolved in 0.5 ml $H_2O$, and treated again with phenol/chloroform/isoamylalcohol (25:24:1, v/v) and chloroform/isoamylalcohol (24:1, v/v) before precipitation. Finally, the RNA pellet was dissolved in 100 μl $H_2O$.

Alternatively, samples are frozen and ground with 100 mM Tris (pH 9) and phenol in liquid nitrogen in a mortar and pestle as described in Haffier et al. (1978) Can. K. Biochem. 56:7229–7233. The emulsion is centrifuged; the aqueous layer is removed, mixed with 2.5 volumes with ice-cold ethanol for 1 hour at 4° C., then recentrifuged. The RNA pellet is washed and resuspended for further analysis.

Northern Analysis. A sample of the RNA, from 1–20 μg can be loaded onto a 1.2% agarose gel containing 6.5% formamide and 20 mM MOPS (pH 7.0), 8 mM sodium acetate, 1 mM EDTA. The gel is electrophoresed at 120 V for approximately 2 hours or until adequate separation is achieved. The gel is then placed on a nitrocellulose filter and blotted overnight using 2×SSC (17.3 g sodium chloride, 8.82 g sodium citrate pH 7.0 per 1 L) and a wick made of Whatman 3MM paper. After blotting, the filter is rinsed and crosslinked with ultra-violet light. The activity of a sporamin-related promoter is then detected using a nucleic acid probe synthesized from isolated sporamin-related cDNA, or, if the promoter is operably linked to a heterologous gene, then the heterologous gene is used as the probe. The probe DNA is denatured and random primers are annealed to it. The mixture is then incubated with Klenow DNA polymerase, $^{32}$P-dATP, dCTP, dGTP, and dTTP. Alternatively, the probe can be produced by PCR using appropriate primers and $^{32}$P-dATP. The radiolabeled nucleic acid probe is purified, e.g., using a spin column. The probe is then denatured and combined with the filter in hybridization buffer consisting of 18% formamide, 5×SSC, 5×Denhardt's Solution, 1% SDS, and 100 μg/ml denatured salmon sperm DNA (Sigma). After 8–18 hours of incubation at 42° C., the hybridization buffer is removed, and the filter is washed two to three times at 65° C. with 2×SSC. The filter is then dried and autoradiographed. mRNAs for the sporamin gene or a heterologous gene appear as bands on an autoradiogram.

Reporter Genes. In an exemplary embodiment, a promoter is operably linked to a reporter gene. Reporters can include β-glucuronidase (GUS), green fluorescent protein (GFP), luciferase, B protein which regulates anthocyanin pigment production (Goff et al. (1990) EMBO J. 9:2517–2522), and chloramphenicol acetyltransferase (CAT). Additional reporter genes are described, e.g., in K. Weising et al., Ann. Rev. Genetics, 22:421, 1988. The GUS (β-glucuronidase) gene, this nucleic acid can then be introduced into plants and plant cells as described below. The expression pattern of the GUS gene provides a direct "report" or evidence of the ability of a promoter to regulate heterologous gene transcription. The expression pattern of the GUS gene is easily assayed. A qualitative, but spatially and temporally accurate view of the expression pattern is produced by obtaining tissue samples and sections, and applying the histochemical stain X-gluc (5-bromo-4-chloro-3-indolyl-beta-d-glucuronic acid) which is converted to a chromogenic product by GUS. Visible staining of cells and tissues is indicative of promoter activity. Alternatively, a quantitative analysis can be performed using 4-methylumbelliferyl-β-D-glucuronide substrate which is hydrolyzed by the GUS reporter enzyme, and which can be easily followed using a spectrophotometer. The assay is described below.

Construction

The promoters of the invention can be incorporated into vector. Vectors, such as expression vectors, can be used to propagate the promoter sequence in bacteria. In this context, it is noted that the promoter sequence can be separated from a heterologous sequence during the propagation step. Vectors can be viral vectors in which the nucleic acids of the invention are ligated into viral genomes. Some vectors, e.g., viral vectors, are integrated into the genome of a host cell upon introduction into the host cell, and are thereby replicated along with the host genome. Other vectors are capable of autonomous replication in a host cell into which they are introduced. For example, bacterial vectors can have a bacterial origin of replication, e.g., the E. coli ori sequence, and an antibiotic resistance gene, e.g., the bla gene encoding ampicillin resistance. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, particle bombardment, or electroporation.

Promoters can be cloned into a bacterial cloning vector, e.g., pUC19, pBR322, or pBluescript (Stratagene). Furthermore, the synthesis of specially designed oligonucleotides in combination with PCR can allow the generation of restriction enzyme cleavage sites at a desired location in the promoters. For example, convenient restriction sites can be engineered at either terminus of a promoter to facilitate cloning into a vector. Moreover, a restriction site can be placed at or near the start codon of the a coding sequence, or, alternatively, following a signal sequence. In yet another variation, a series of restriction sites, also termed a "polylinker," can be inserted such that the restriction sites are unique in the resulting plasmid. In subsequent manipulations, a desired heterologous gene, for example, one described herein, can be easily inserted into the vector such that it is operably linked to a promoter.

Such a vector is referred to as an expression vector, since it is capable of directing the expression of genes to which a promoter is operatively linked. In addition to a promoter, an expression vector can optionally further include: a 5' untranslated region, a signal sequence, a transit peptide, an intron, a 3' untranslated region, a polyadenylation site, and a 3' regulatory sequence. A signal peptide directs the recombinant protein into the endoplasmic reticulum, vacuole, or extracellular space. A suitable signal peptide is that of αAmy8 (Chan et al. (1994) *J. Biol. Chem* 269:17635–17641) and that of the sporamin gene itself (see GenBank entry GI:604320). A transit peptide directs the protein to a subcellular compartment, e.g., nucleus, chloroplast, vacuole, or mitochondria. Example of suitable terminator sequences and polyadenylation signals are contained in the *A. tumefaciens* nos gene and the rice α-amylase gene.

The vector can further include an enhancer and/or a 5' regulatory sequence. One skilled in the art can construct a chimeric promoter, of which one component is the a fragment of a promoter of the invention. Methods for constructing chimeric promoters are routine in the art (see e.g., Fluhr et al. (1986) *Science* 232:1106–1112; Strittmatter and Chua (1987) *Proc Natl Acad Sci USA* 84:8986–8990; Comai et al. (1991) *Plant Molec. Biol.* 15:373–381.). For example, a fragment of a sporamin-related promoter, e.g., a fragment with wound-responsive elements, can be attached to the 5' end of a truncated second plant promoter which is selected to provide the TATA element and mRNA start site. Recombinant techniques are used to manipulate the nucleic acid fragments to obtain the desired construction. In another example, the two promoters are reversed, i.e., a truncated sporamin-related promoter provides the TATA element and mRNA start site, while elements from a second promoter are attached to the 5' end of the truncated sporamin-related promoter. Examples of a second promoter include the ribulose-bisphosphate carboxylase small subunit promoter, β-conglycinin promoter, phaseolin promoter, ADH promoter, heat shock protein promoters, and tissue specific promoters, and the like. Chimeric promoter, such as the ones described above, can also be designed to combine desirable regulatory elements.

A vector including the sporamin promoter can further include sequences to facilitate introduction of the promoter into plant cells. The vector can have features for the stable integration of the vector or fragment thereof into plant genome. A vector can have a selectable marker to identify transformed plant cells against a background of untransformed cells. Selectable markers can include the aminoglycoside phosphotransferase gene of transposon Tn5 (Aph II), which encodes resistance to the antibiotics kanamycin, neomycin, and G418. Other selectable markers are available which encode resistance or tolerance to glyphosate, hygromycin, methotrexate, phosphinothricin, imidazolinones, sulfonylureas, and triazolopyrimidine herbicides, such as chlorosulfuron, bromoxynil, dalapon, and the like. In addition to a selectable marker gene, it may be desirable to use a reporter gene, e.g., one described above in order to identify transformed cells. In some instances a reporter gene may be used with a selectable marker.

Heterologous Nucleic Acids

Promoters of the invention can be used to direct the expression of heterologous nucleic acids. These nucleic acids can encode polypeptides and RNAs such as anti-sense RNA and ribozymes. Moreover, the encoded polypeptides can be biosynthetic enzymes which produce a desired metabolite. An anti-sense RNA is complementary to a target mRNA. One skilled in the art can design an anti-sense RNA which hybridizes to its target and inhibits translation of the target mRNA. A ribozyme is a catalytic RNA which can specifically cleave substrate, e.g., another nucleic acid. A skilled artisan can design a ribozyme to cleave a desired mRNA transcript, and thus, inactivate it. For example, group I, axhead, hairpin, hammerhead, and RNase P ribozymes are suitable model molecules for ribozyme design (see Castanotto et al. (1994) *Advances in Pharmacology* 25:289).

Encompassed by the present invention are nucleic acids in which the promoters of the invention direct production of heterologous products, such as polypeptides and nucleic acids, to the tuber, to damaged or infected leaves, or to elicitor treated plants.

The tubers of the sweet potato are a natural storage reservoir. Further, the principle protein component in these stores is sporamin. Thus, a sporamin-related promoter, allows one to direct the production of a heterologous polypeptide, nucleic acid, or metabolite in the tubers. Unexpectedly, the promoter is also induced in the leaves of plants in response to injury and to an elicitor, e.g., methyl jasmonate. Hence, the promoter can be used to produce any heterologous polypeptides, nucleic acids, or metabolites, in leaves upon injury or upon application of an elicitor.

A heterologous polypeptide can be a protein of pharmaceutical or medical utility. Such proteins can include: peptide hormones; cytokines; growth factors; carrier proteins (e.g., ferritin, transthyretin); antibodies, including humanized antibodies, single-chain antibodies, and chimeric antibodies; blood plasma proteins; enzymes including clotting factors, and metabolic enzymes; antigens, such as vaccine components; and structural proteins such as collagens, fibrinogen, and intermediate filaments. These proteins can be of human, mammalian, or synthetic origin. The production of antibodies or fragments thereof (Hiatt et al. (1989) *Nature* 342:76–78; Hein et al. (1991) *Biotechnol. Prog.* 7:455–461), serum albumin (Sijmons et al. (1990) *Bio/Technology* 8:217–221), cytochrome P450 (Saito et al. (1991) *Proc Natl Acad Sci USA* 88:7041–7045), hepatitis B surface antigen (Mason et al. (1992) *Proc Natl Acad Sci USA* 89:11745–11749), human interferon (de Zoeten et al. (1989) *Virology* 172:213–222) has been reported.

In addition, the sporamin promoter can regulate the expression of an enzyme, for example, an enzyme of agricultural or industrial utility. Such enzymes can include proteases, cellulases, lignases, amylases, pectinases, and phytases. Lytic and processing enzymes can be utilized to obtain useful and consumable products from indigestible or low quality plant materials. Such products can be used as chemical feedstocks, nutritional supplements, or food additives. The sporamin promoter can regulate the expression of heterologous biosynthetic enzymes for the production of secondary metabolites in plant cells. For example, the promoter can be engineered to produce a series of enzymes to replicate a biosynthetic pathway. Secondary metabolites of particular utility can include: alkaloids, isoprenoids (e.g., carotenoids and the like), antibiotics, steroids, complex carbohydrates, and plastics (e.g., polyhydroxyalkanoates, such as polyhydroxybutyrate).

The promoter and derivatives thereof can be utilized to direct the synthesis of any of the aforementioned proteins in a "post-harvest" production regime. This method is of particular advantage when the desired products are labile or harmful to the plant host. In this regimen, the desired products are not produced during the normal growth of the plant, but when the plant or plant part, e.g., leaf, is mechanically macerated and/or treated with an elicitor, such as methyl jasmonate, shortly before, during, or after harvesting. Alternatively, the plant can be treated with a pathogen. A suitable time interval between harvesting and the event of wounding and/or elicitor treatment can be determined and optimized without undue experimentation by one skilled in the art. The levels of the desired product can be detected, e.g., by antibody-based ELISA assays, mass spectroscopy, nucleic acid hybridization, etc., at various times after the event of wounding and/or elicitor treatment.

Post-harvest production can also be applied to plant cells grown in culture, for example callus cultures. These cultures can similarly be wounded and/or treated with an elicitor (see, e.g., *Handbook of Plant Cell Culture,* Vol. 4, "Techniques and Applications", Evans, D. A., Sharp, W. R. and Ammirato, P. V., 1986 Macmillan Pub., New York, N.Y.).

The invention provides means of enhancing the resistance of a plant to pathogens and environmental insults. The promoter of the invention and derivatives thereof are activated by plant cell wounding, exposure to pathogens, or environmental insult. The promoter can be operably linked to a heterologous sequence which produces, directly or indirectly, agents to enhance plant defenses, to counteract deleterious effects of injury or infection, and/or to inactivate pathogens.

Viral pathogens. Defense against viral pathogens can be provided (see, e.g., Gadani et al. (1990) *Arch. Virol.* 115: 1–21). The present invention encompasses nucleic acids sequences comprising a promoter operably linked to sequences encoding a virus coat protein, an anti-sense RNA complementary to a viral RNA, and/or a ribozyme which selectively targets a viral RNA. The production and accumulation of viral coat proteins in plant cells provides resistance to viral infection and reduces viral disease progression when the coat protein is derived from the infecting virus, e.g., alfalfa mosaic virus, cucumber mosaic virus, tobacco streak virus, potato virus X, potato virus Y, tobacco etch virus, tobacco rattle virus, and tobacco mosaic virus (see Beachy et al. (1990) *Ann. Rev. Phytophathol.* 28:451–474). Another method of protecting against viruses entails fusing the promoter to the mammalian 2'-5' oligoadenylate synthase gene. Expression of this enzyme protects plants against viral infection under field conditions (Truve et al. (1993) *Bio/Technology* 11:1048–1052).

Alternatively, the sporamin promoter can direct the transcription of an antisense RNA or ribozyme to counteract viral pathogens. Antisense RNA has been demonstrated to confer resistance against the cucumber mosaic virus (Rezaian et al.(1988) *Plant Molec. Biol.* 11:463–471) and tomato mosaic virus (Day et al. (1991) *Proc Natl Acad Sci USA* 88:6721–6725). One skilled in the art without undue experimentation can design and/or test the efficacy of antisense RNAs complementary to a viral mRNA or fragment thereof. In addition to antisense inhibition, sense suppression can be used to inhibit mRNA expression (see U.S. Pat. No. 5,034, 323).

Ribozymes are catalytic RNA molecules useful for inhibiting gene expression. A ribozyme can be targeted against an mRNA, e.g., a plant cell mRNA and/or a viral RNA. The ribozyme can specifically recognize the sequence and/or structure of a target RNA and cleave the phosphodiester backbone at a specific site. As a catalyst, the ribozyme itself is not altered, is recycled, and cleaves additional targets. One class of ribozymes is derived from small circular RNAs. These ribozymes are capable of self-cleavage and replication in plant cells. Viroid-based ribozymes are competent to replicate alone, whereas satellite RNA-based ribozymes require a helper RNA, e.g., from tobacco ringspot virus, *Solanum nodiflorum* mottle virus, velvet tobacco mottle virus, and lucerne transient streak virus. An example of a viroid RNA is the avacado sunblotch viroid. Methods for constructing ribozymes are known in the art (see above).

Bacterial Pathogens. A promoter of the invention can be used to drive the expression of sequences that defend against bacterial pathogens in wounded or infected tissues. Such sequences can encode thionins, cecropins, maganins, and lysozymes.

Fungal Pathogens. Similarly, fungal pathogens can be defended with genes encoding glucanases, chitinases, and zymolases. Chitin and glucans, the substrates for these enzymes, are integral components of cell wall of fungi. Weakening the cell wall by digestion of these components with heterologous enzymes retards fungal pathogenesis (e.g., see U.S. Pat. No. 4,94,840). Expression of a fungal ribosome inactivating protein has anti-fungal properties (Leah et al. (1991) *J Biol Chem* 266:1564–1573). Thus, the expression of this protein may be beneficial. In addition, fungi utilize enzymes, such as endo α-1,4-D-polygalacturonases, to solubilize the plant cell well materials for nutrients. Polypeptide inhibitors of fungal endopolygalacturonases can be operably linked to the sporamin promoter to antagonize fungal pathogenesis (Toubart et al. (1992) *Plant J.* 2:367–373).

Animal Pathogens. If the plant is vulnerable to insect and nematode pathogens, the promoter can be operably linked to genes encoding Bt (*Bacillus thuringiensis*δ-endotoxins), protease inhibitors, collagenases, chitinase, glucanases, lectins, glycosidases, and neurotoxins. For example, cyrIA δ-endotoxins are highly toxic to lepidopteran insects, while cyrIIIA δ-endotoxins are highly toxic to coleopteran insects. The sequences and methods of using δ-endotoxins are well known in the art (Geiser et al. (1986) *Gene* 48:109–118; Williams et al. (1992) Bio/Technology 10:540–543; Koziel et al. (1993) Bio/Technology 11:194–200; Fujimotom et al. (1993) Bio/Technology 11:1151–1155; Lereclus et al. (1992) Bio/Technology 10:418–421). Chitin is an key component of the outer casing of nematodes, nematode eggs, and nematode cysts. Thus, chitin degrading enzymes such as chitinases provide protection against nematodes.

Environmental Insult. To provide additional defense against injuries caused by environmental insult, a promoter of the invention can be operably linked to a heat shock protein, cytochrome P450, superoxide dismutase, or glutathione reductase. For example, resistance to certain herbicides can be conferred by a chimeric protein derived from rat cytochrome P4507A1 and yeast NADPH-cytochrome P450 oxidoreductase (Shiota et al. (1994) *Plant Physiol* 106:17). Expression of an acetohydroxy acid synthase (Hattori et al. (1995) *Mol. Gen. Genet.* 246:419) and a phosphotransferase (Datta et al. (1992) *Plant Mol. Biol.* 20:619) were also shown to impart herbicide resistance. Thus, to provide herbicide resistance, the sporamin promoter can be operably linked to any one of these proteins or functional fragments thereof. One advantage of utilizing the promoter in defense against viruses, bacteria, insects, and nematodes is that the agent is only expressed at the time and in the tissue where the response is required, thus conserving resources in the plant and preventing undue effects of constitutive production of the agent.

Methods of Transforming Plant Cells

A nucleic acid construct of the present invention can be transformed into a plant cell to produce a desired transgenic plant or plant cell. Methods for transforming plant cells with nucleic acid are routine in the art. Further, the plant cells can be transformed with multiple constructs, e.g., sequentially or concurrently. Depending on the desired physiological and agronomic properties of a plant species, and the nucleic acid construct of the present invention, a target plant or plant cell for transformation can include a species from maize, wheat, rice, soybean, tomato, tobacco, carrots, peanut, potato, sugar beets, sunflower, yam, *Arabidopsis,* rape seed, sunflower, and petunia.

One implementation of the current invention utilizes *Agrobacterium* to introduce the desired construct into plant cells U.S. Pat. Nos. 5,177,010, 5,104,310, 5,149,645, 5,469,976, 5,464,763, 4,940,838, 4,693,976, 5,591,616, 5,231,019, 5,463,174, 4,762,785, 5,004,863, and 5,159,135; and European Patent Applications 116718, 290799, 320500, 604662, 627752, 0267159, and 0292435). The method can be used with both dicotyledonous plants cells (Bevan et al. (1982) *Ann. Rev. Genet.* 16:357–384; Rogers et al. (1986) *Methods Enzymol.* 118:627–641), and monocotyledonous plant cells (Hemalsteen et al. (1984) *EMBO J* 3:3039–3041; Hooykass-Van Slogteren et al. (1984) *Nature* 311:763–764; Grimsley et al. (1987) *Nature* 325:1677–179; Boulton et al. (1989) *Plant Mol. Biol.* 12:31–40.; Gould et al. (1991) *Plant Physiol.* 95:426–434). The method employs binary *Agrobacterium* T-DNA vectors (Hoekema et al. (1983) *Nature* 303:179; Bevan (1984) *Nucl. Acid Res.* 12:8711–8721), and co-cultivation procedures (Horsch et al., (1985) *Science* 227:1229–1231).

The desired nucleic acid construction, for example, a sporamin-related promoter operably linked to a heterologous gene, is ligated into a binary vector, between the left and right border sequences of T-DNA. The binary vector further includes an Hph gene coding for hygromycin resistance. The binary vector containing the desired construction is transformed into an *E. coli* strain, e.g., DH5α. Subsequently the binary plasmid is transferred into an *Agrobacterium,* e.g., *Agrobacterium* strain LBA4404, using a triparental mating.

Leaf discs are prepared from axenically grown tobacco seedlings. The discs are incubated for 8 hours on sterile filter papers overlayed on tobacco nurses cells on a feeder plate containing modified MS medium with Nitsch vitamins, 100 ml/L myo-inositol, 30 mg/L sucrose, 0.4 mg/L BAP, 1 mg/L 2,4-D (dichlorophenoxyacetic acid), 8 ml/L agar. To establish co-cultivation, the filters bearing the leaf disks are submersed in a suspension of the *Agrobacterium* bearing the desired binary vector, the bacteria being a concentration of approximately $1 \cdot 10^9$ cell/ml, and vacuum infiltrated (3×1 minute). The filters and leaf discs are incubated on the nurse plate for 48 hours at 25° C. with indirect light. The discs are transferred to selection/regeneration plates containing MS salts, Nitsch vitamins, 100 ml/L myo-inositol, 20 g/L sucrose, 2 mg/L zeatin, 4 g/L agar, 500 μg/ml carbemicillin and an appropriate antibiotic, e.g., G418 to select for the hygromycin resistance gene. The plates are placed in a growth chamber at 25° C. for 18 hours with light. The resulting shoots are transferred to rooting media, grown into plantlets, transferred to soil, and grown into plants in a green hose. One skilled in the art can adapt this method to transform other species of plants.

Other methods for transforming plant cells are available. Of particular utility for transforming monocotyledonous plants or plant cells are methods of protoplast transformation. The details of such methods are known to artisans of ordinary talent. Protoplasts can be isolated from a suspension culture of potato stems, e.g., from the Datura variety of *Solanum tubersoum.* Approximately 20 μg of highly purified plasmid DNA is transformed into the cells using the $CaCl_2$/PEG method. For example, a plasmid containing the sporamin promoter and an operably linked heterologous sequence can be introduced into protoplasts by methods known to one of ordinary talent in the art. Expression can be analyzed. Methyl jasmonate can be added prior to expression analysis. The plasmid can be similarly introduced into protoplasts from other plant species, such as tobacco, parsley, and rice.

These additional methods include but are not limited to, protoplast transformation through calcium-, polyethylene glycol (PEG)—or electroporation-mediated uptake of naked DNA (see Paszkowski et al., 1984, *EMBO J* 3:2717–2722, Potrykus et al. 1985, *Molec. Gen. Genet.* 199:169–177; Fromm et al., 1985, *Proc. Nat. Acad. Sci. USA* 82:5824–5828; Shimamoto, 1989, *Nature* 338:274–276), microinjection, silicon carbide mediated DNA uptake (Kaeppler et al., 1990, *Plant Cell Reporter* 9:415–418), and microprojectile bombardment (see Klein et al., 1988, *Proc. Nat. Acad. Sci. USA* 85:4305–4309; Gordon-Kamm et al., 1990, *Plant Cell* 2:603–618), whiskers technology (see U.S. Pat. Nos. 5,302,523 and 5,464,765), and viral vector systems (see, U.S. Pat. Nos. 5,316,931, 5,589,367, 5,811,653, and 5,866,785).

Assaying Promoter Functionality

In order to assay the functionality of a promoter of the invention, a plant cell, tissue, or organism can be subjected to wounding conditions, pathogens, pests, or field trials. The subjected plant can then be assayed for expression of a nucleic acids sequence operably linked to the promoter. The following respectively describe methods of determining if the promoter responds to a bacteria pathogen, a fungal pathogen, a nematode pest, and a variety of insults present in field conditions.

Bacteria. A culture of *Erwinia carotovora* ssp. *carotovora,* strain EC14, causal agent of soft rot can be grown in LB media at 25° C. The culture is pelleted, and resuspended in sterile distilled water ($OD_{600}$=~3.0). Transgenic tobacco leaves bearing a promoter-GUS transgene are excised at the petiole, and placed on a moist filter paper in a petri dish. The leaf is wounded gently on the top face with a tip of a micropipettor and 2 ml of either sterile, distilled water, i.e. a negative control, or 2 ml of the EC14 *Erwinia* culture were pipetted onto the wound. The petri plates are closed and sealed to prevent evaporation, and incubated at 28° C. in the dark. Samples are taken every 24 hours by excising a leaf section surrounding the inoculation site with a hole punch or cork borer. The sample is analyzed with a histochemical method described herein.

Fungi. Seeds of transgenic tobacco bearing the promoter-GUS transgene are surface-sterilized with 30% bleach and then washed extensively with sterile water and potted in autoclaved potting mix. An oat seed infested with the fungus *Rhizoctonia solani,* e.g., strains RS51 or R992, are contacted to the seed hypocotyls of the tobacco seedlings. Every approximately 24 hours, an infected seedling is removed. The soil is cleaned off with sterile water, and the seedling is processed for histochemical staining for GUS activity as described herein.

Nematodes. Transgenic seedlings can be grown on seed germination media for 10 days. Nematodes, e.g., *Melodigyne igcognita* or *M. hapla,* can be applied onto the media. The seedlings are harvested at about 0, 1, 2, 3, 5, and 7 days after inoculation. Roots can be analyzed for GUS expression from the promoter-GUS transgene.

Field Test. Seedlings of transgenic tobacco bearing the promoter-GUS transgene can be planted, e.g., in a greenhouse or in a pot in a growth chamber. After growth, plants can also be grown in the field. Leaves of the grown plants can be contacted with natural pathogens such as cyst nematodes, aphids, beetles, and hornworms. The plants can alternatively be exposed to tobacco mosaic virus. Samples are obtained at regular intervals for analysis, e.g., histochemical staining for GUS activity as described herein.

Methods for Applying an Elicitor

An elicitor can be used to activate the sporamin promoter in a controlled manner. An elicitor may be applied to plant tissues, e.g., leaves, either by direct contact or by supplying a volatile or airborne source.

In the former case, the elicitor is prepared in a solution, e.g., an aqueous solution, at a concentration from about 1 ng/ml to 100 mg/ml, about 1 ng/ml to 1 mg/ml, or about 1 µg/ml to 1 mg/ml. The solution can comprise an organic solvent, e.g., glycerol or ethanol. Alternatively, the elicitor can be formulated with one or more agriculturally acceptable carriers. Agricultural carriers can include: clay, talc, bentonite, diatomaceous earth, kaolin, silica, benzene, xylene, toluene, kerosene, N-methylpyrrolidone, alcohols (methanol, ethanol, isopropanol, n-butanol, ethylene glycol, propylene glycol, and the like), and ketones (acetone, methylethyl ketone, cyclohexanone, and the like). The formulation can optionally further include a stabilizer, spreading agent, wetting extenders, dispersing agents, sticking agents, disintegrators, and other additives, and can be prepared as a liquid, a water-soluble solid (e.g., tablet, powder or granule), or a paste.

Prior to application, the solution can be combined with another desired composition such as insecticide, germicide, fertilizer, plant growth regulator and the like. The solution may be applied to the plant tissue, for example, by spraying, e.g., with an atomizer, by drenching, by pasting, or by manual application, e.g., with a sponge. The solution can also be distributed from an airborne source, e.g., an aircraft or other aerial object, e.g., a fixture mounted with an apparatus for spraying the solution, the fixture being of sufficient height to distribute the solution to the desired plant tissues. Alternatively, the elicitor can be applied to plant tissue from a volatile or airborne source. The source is placed in the vicinity of the plant tissue and the elicitor is dispersed by diffusion through the atmosphere. The source and the plant tissue to be contacted can be enclosed in an incubator, growth chamber, or greenhouse, or can be in sufficient proximity that they can outdoors.

In another implementation, if the elicitor is distributed systemically thorough the plant, the elicitor can be applied to tissues other than the leaves, e.g., to the stems or roots. Thus, the elicitor can be distributed by irrigation. The elicitor can also be injected directly into roots or stems.

Elicitors contemplated by the current invention include methyl jasmonate, jasmonic acid, and derivatives thereof. A derivative of jasmonic acid can include 7-iso-jasmonic acid, 9,10-dihydrojasmonic acid, 2,3-didehydrojasmonic acid, 3,4-didehydrojasmonic acid, 3,7-didehydrojasmonic acid, 4,5-didehydrojasmonic acid, 5,6-didehydrojasmonic acid, 6,7-didehydrojasmonic acid, and 7,8-didehydrojasmonic acid. Also contemplated are lower alkyl esters and stereoisomers of methyl jasmonate and its derivatives. Further, methyl jasmonate or it derivatives can be conjugated to carrier ligand. Another elicitor contemplated by the current invention is abscisic acid. Methyl jasmonate and abscisic acid can be obtained from a commercial supplier (e.g., Sigma, St. Louis Mo.).

A kit

The present invention also features a kit which includes a vector nucleic acid bearing a sporamin-related promoter. A restriction enzyme polylinker can be 3' of the promoter, and can include recognition sites for restriction enzymes, e.g., type II restriction enzymes, preferably ones which do not recognize other sites in the vector, i.e., the sites are unique. The vector can optionally include a 5' untranslated region, a signal sequence, a 3' untranslated region, a polyadenylation site, a 3' regulatory region, a T-DNA left and right border sequence, and a selectable marker for selection of transformed plant cells. The kit can optionally further include instructions for use, *Agrobacterium* for transformation, an elicitor, plant seeds, and/or plant cells.

Without further elaboration, it is believed that the above description has adequately enabled the present invention. The following examples are, therefore to be construed as merely illustrative, and not limitative of the remainder of the disclosure in any way whatsoever. All of the publications cited herein are hereby incorporated by reference in their entirety.

Results

Cloning, Sequencing, and Sequence Analysis of the *Ipomoea batatas* Sporamin Promoter The sporamin promoter was isolated from sweet potato genomic DNA using the primer walking method as described in Siebert et al. (1995) supra. A primer was designed based on the sequence of known sporamin genomic DNA. A 21 base oligonucleotide, GSP2 (5'-GAACTTGGGAGAAAAGCTAAG-3', SEQ ID NO:3) was synthesized. The GSP2 primer was used to amplify the 5' flanking sequence of the sporamin gene from genomic DNA of the sweet potato *Ipomoea batatas* cv. Tainung 57 using the primer walking method described in Siebert et al. (1995) supra). The amplified 1.25 kb DNA fragment was ligated into the SmaI site of the pUC19 vector. The ligation product was transformed into *E. coli* XL1Blue cells. Plasmid DNA was purified from a clone containing the 1.25 kb insert. The nucleotide sequence of the insert was determined by the dideoxynucleotide termination method. The sequence of the 1.25 kb promoter region is recited in SEQ ID NO:1.

The promoter was analyzed for possible signal response elements using the Wisconsin GCG software package 9.0 (available at http://www.gcg.com/; Devereux et al. (1984) *Nucleic Acids Res.* 12:195–387). The following elements were identified: (1) a sucrose response element, "TGGACGG" located at about nucleotides −296 to −302 of SEQ ID NO:1; (2) a SP8a box, "ACTGTGT," located at about nucleotides −145 to −151 of SEQ ID NO:1; (3) a PI-II wound response element located at about nucleotides −770 to −781 of SEQ ID NO:1 ("CGAAAGCACCTT"; SEQ ID NO:4); (4) an element similar to the nos wound response element located at about nucleotides −1084 to −1094 of SEQ ID NO:1 ("GTAAAATACGTA"; SEQ ID NO:5); (5) an element similar to the G-box element was located at about nucleotides −1114 to −1119 of SEQ ID NO:1.

Expression Pattern of the Sporamin Gene in Sweet Potato

Total RNA was extracted utilizing the rapid guanidinium hydrochloride-sarcosinate method as described in (Yeh et al. (1991) *Focus* 13:102–102.) The sporamin cDNA was radio-labelled with $^{32}$p dATP and used as a hybridization probe for Northern analysis as described above.

Sweet potato plants (*Ipomoea batatas* cv. Tainung 57) were grown in pots at 28° C. with 16 hour of light (2000 lux) and 8 hours of darkness per day. Total RNA was extracted from leaves and stems of mature plants, tubers, 1–2 cm sprouts, and 3–5 cm sprouts. 5 µg of total RNA from the tubers, and 15 μg from the sprouts and mature plant were electrophoresed on an agarose gel, and blotted onto a filter. The filter was hybridized with radiolabelled sporamin cDNA, washed, and then autoradiographed. Tubers expressed the highest levels of the sporamin gene, with moderate levels in sprouts, and little if any in the leaves and stems of mature plants. In addition, trypsin inhibitory activity was assayed in 10 μg of soluble crude protein from each above sample following the method of Yeh et al. ((1997) *Plant Mol. Biol.* 33:565–570).

Sporamin gene expression was characterized in wounded plants. A scissors was used to wound the middle of leaves from sweet potato plants of approximately 10 cm in height. A sample was obtained at 0, 2, 4, and 8 hours after wounding by dissecting 1.5 cm strips of leaf tissue from wounded and unwounded plants with a razor. Total RNA was extracted as described above. 15 μg of leaf RNA and 5 μg of tuber RNA were loaded on agarose gels and assayed for sporamin gene expression using the Northern analysis procedure described above. The level of sporamin gene expression increases markedly in response to wounding in mature leaves. Progressively more sporamin RNA is detected with the most being observed 8 hours after wounding.

Tissue-Specific Expression Pattern of the Sporamin Promoter

To analyze the properties of the sporamin promoter, the promoter was operably linked to the reporter gene β-glucuronidase (GUS). The plasmid pBI101 is a Ti plasmid binary vector harboring the GUS gene in a form lacking a promoter (Clontech, Palo Alto Calif.). The sporamin promoter was excised with the restriction endonucleases XbaI and BamHI, isolated, and ligated into compatible sites of a restricted pBI101 nucleic acid. The resulting plasmid construct, termed pBI101/Pspoa, was verified by restriction mapping and nucleic acid sequencing.

The plasmid was transformed into tobacco cells (*Nicotiana tabaccum* cv. W38) using *Agrobacterium tumefaciens* LBA4404 in the leaf disc method (Hörsch et al. (1985). *Science* 227:1229–1231). Multiple transformed lines harboring the pBI101/Pspoa construct were obtained. Two lines, Tspoa11 and Tspoa37 were selected for further analysis. GUS activity was measured in the leaves of plants obtained from these lines as follows. A middle leaf of the mature tobacco plant was injured with a scissors. Two hours later, wounded and unwounded leaves were harvested, mixed with GUS extraction buffer (50 mM sodium phosphate, pH 7.0, 10 mM EDTA, 10 mM β-mercaptoethanol, 0.1% sodium lauryl sarcosine, 0.1% Triton X-100), frozen, and grounded into a fine powder with a mortar and pestle while in liquid nitrogen. The sample was thawed and centrifuged at 12,000×g for 10 minutes at 4° C. The total protein content was determined using the method of Bradford ((1976) *Anal. Biochem.* 72:248–254). GUS activity was measured in a fluorometric assay by the addition of 4-methylumbelliferyl-β-D-glucuronide substrate and monitoring the reaction in a spectrophotometer to determine Miller units (MU) of activity following the method of Jefferson ((1987) *EMBO J* 6:3901–3908). The two tobacco plants bearing the Pspoa-GUS fusion transgene each exhibited marked induction of the GUS reporter gene upon wounding (Table 1).

TABLE 1

Pspoa-GUS Activity in Response to Wounding.

| Plant Line | GUS activity (nmole MU/min/mg protein) | |
|---|---|---|
| | Without Wounding | With Wounding |
| Wildtype | <5 | <5 |
| Pspoa 11 | 45 | 255 |
| Pspoa 37 | 20 | 260 |

Thus, the sporamin promoter is able to regulate a heterologous gene, the GUS reporter gene. This regulation, moreover, is responsive to wounding to leaves of mature tobacco plants. The experiment demonstrates that the sporamin promoter is functional in tobacco plants, and thus, is a useful for regulating gene expression in a broad class of plants, not just tuberous plants.

Induction of sporamin promoter was observed over time. GUS activity was monitored as described above at various intervals after leaf wounding. GUS expression was rapidly induced within 15 minutes of wounding. The level of expression rapidly increased to over 250 nmole MU/min/mg of protein within 2 hours. GUS expression remained above this level for at least 50 hours after wounding, with a maximum at 12 hours after wounding. The maximum expression level was 16 fold over the uninduced (i.e., unwounded) level of GUS expression.

The localization of the Pspoa-GUS fusion expression was determined by histochemical staining of leaves for GUS activity as follows. Leaves were sectioned with a razor blade. The excised tissues were stained for GUS activity, as described in Jefferson et al. (1987), supra. The tissue sections were incubated with 1 mM 5-bromo-4-chloro-3-indolyl β-D-glucoronide (X-gluc) at 37° C. Robust GUS activity was observed in wounded leaves, and also in unwounded leaves of the same plant. The level of GUS activity was at least 4–7 fold higher than in wounded leaves than unwounded leaves. Particularly high levels of GUS expression were observed in the lower stems of the plant. In contrast to the aerial regions of the plan, no GUS expression was induced by wounding in the roots. GUS activity was observed in the meristem regions irrespective of wounding, indicative of developmental activation of the sporamin promoter.

Effects of Methyl Jasmonate

The activity the Pspoa-GUS fusion was monitored in response to spraying with the elicitor, methyl jasmonate. Solutions of 50 μM and 100 μM methyl jasmonate were prepared and sprayed onto leaves using a commercial atomizer. Sodium phosphate buffer, pH 7.0, was used as a control solution. GUS activity increased 37 fold two hours after spraying with 50 μM methyl jasmonate and 20 fold two hours after spraying with 100 μM methyl jasmonate. Histochemical straining revealed that activation was restricted to the aerial regions of the plant. Similar results were obtained using a quantitative fluorometric assay (Table 2).

TABLE 2

Pspoa-GUS Activity in Response to Elicitors.

| Treatment | GUS activity (nmole MU/min/mg protein) |
| --- | --- |
| Unsprayed control | <20 |
| Wounding | 440 |
| Sodium phosphate buffer control | <20 |
| 50 μM methyl jasmonate | 420 |
| 100 μM methyl jasmonate | 225 |
| 100 μM ABA | 170 |
| 200 μM ABA | 60 |
| 200 μM SA | 15 |
| 1 mM SA | 21 |

Effects of Abscisic Acid

The activity of the sporamin promoter fused to the GUS reporter gene was monitored in response to abscisic acid (ABA). Solutions of 100 μM and 200 μM ABA were prepared and sprayed onto leaves using a commercial atomizer. A fluorometric assay indicated that 100 μM ABA was a potent inducer of the sporamin promoter (Table 2). Treatment with salicylic acid (SA) or ethylene, however, had no effect on the sporamin promoter function. However, in assays, where SA treatment precedes wounding of methyl jasmonate treatment, less sporamin promoter activity was observed.

Other embodiments are within the following claims.

---

What is claimed is:

1. An isolated nucleic acid comprising a promoter having a sequence that is at least 95% identical to SEQ ID NO:1 and that comprising a 12 nucleotide site having at least 10 nucleotides identical to SEQ ID NO:5, wherein the promoter directs transcription in response to wounding.

2. An isolated nucleic acid comprising the promoter that comprising SEQ ID NO:1, wherein the promoter comprising a 12 nucleotide site having at least 10 nucleotides identical to SEQ ID NO:5.

3. The nucleic acid of claim 1 further comprising a heterologous sequence, wherein a portion of the nucleic acid containing SEQ ID NO:1 directs transcription of the heterologous sequence.

4. A vector comprising the nucleic acid of claim 1.

5. A transformed bacteria or plant cell comprising the nucleic acid of claim 3.

6. A transgenic plant whose genome comprises the nucleic acid sequence of claim 3.

7. The transgenic plant of claim 6 wherein the plant is a dicot.

8. The transgenic plant of claim 6 wherein the plant is selected from the group consisting of *Ipomoea batatas, Arabidopsis,* rice, tobacco, maize, *Brassica,* and potato.

9. A method of producing a polypeptide, the method comprising:
   providing a tuberous plant having a transgene comprising a promoter having the sequence of the nucleic acid of claim 1, and a heterologous sequence encoding the polypeptide, the heterologous sequence being operably linked to the promoter;
   inducing transcription of the heterologous sequence in a tissue by wounding, pathogen infection, pest infestation, or elicitor treatment;
   harvesting the tissue; and
   recovering the polypeptide from the tissue; to thereby produce the polypeptide.

10. A method of producing a polypeptide, the method comprising:
    providing a plant having a transgene comprising a promoter having the sequence of the nucleic acid of claim 1, and directs expression in tubers, and a heterologous sequence encoding the polypeptide, the heterologous sequence being operably linked to the promoter;

harvesting tubers from the plant; and recovering the polypeptide from the tissue; to thereby produce the polypeptide.

11. The nucleic acid of claim 2 further comprising a heterologous sequence, wherein SEQ ID NO:1 directs transcription of the heterologous sequence.

12. The isolated nucleic acid of claim 11 wherein the heterologous sequence encodes a polypeptide.

13. The isolated nucleic acid of claim 12 wherein the polypeptide is selected from the group consisting of a protease inhibitor, collagenase, chitinase, glucanase, glycosidase, and *Bacillus thuringiensis* δ-endotoxin.

14. A vector comprising the nucleic acid of claim 2.

15. A transformed bacteria or plant cell comprising the vector of claim 14.

16. A transgenic plant whose genome comprises the nucleic acid sequence of claim 11.

17. The transgenic plant of claim 16 wherein the plant is a dicot.

18. The transgenic plant of claim 16 wherein the plant is selected from the group consisting of *Ipomoea batatas, Arabidopsis,* rice, tobacco, maize, *Brassica,* and potato.

19. The transgenic plant of claim 16 wherein the plant is *Ipomoea batatas*.

20. The transgenic plant of claim 16 wherein the plant is tobacco.

21. A method of producing a polypeptide, the method comprising:

providing a tuberous plant having a transgene comprising a promoter having the sequence of the nucleic acid of claim 2, and a heterologous sequence encoding the polypeptide, the heterologous sequence being operably linked to the promoter;

inducing transcription of the heterologous sequence in a tissue by wounding, pathogen infection, pest infestation, or elicitor treatment;

harvesting the tissue; and recovering the polypeptide from the tissue; to thereby produce the polypeptide.

22. A method of producing a polypeptide, the method comprising:

providing a plant having a transgene comprising a promoter having the sequence of the nucleic acid of claim 2, and directs expression in tubers, and a heterologous sequence encoding the polypeptide, the heterologous sequence being operably linked to the promoter;

harvesting tubers from the plant; and recovering the polypeptide from the tissue; to thereby produce the polypeptide.

23. The isolated nucleic acid of claim 3 wherein the heterologous sequence encodes a polypeptide.

24. The isolated nucleic acid of claim 23 wherein the polypeptide is selected from the group consisting of a protease inhibitor, collagenase, chitinase, glucanase, glycosidase, and *Bacillus thuringiensis* δ-endotoxin.

25. The transgenic plant of claim 6 wherein the plant is *Ipomoea batatas*.

26. The transgenic plant of claim 6 wherein the plant is tobacco.

* * * * *